(12) United States Patent
Takabu

(10) Patent No.: US 11,904,158 B2
(45) Date of Patent: Feb. 20, 2024

(54) ADHESIVE SHEET

(71) Applicant: KABUSHIKI KAISYA LEBEN, Yokohama (JP)

(72) Inventor: Atsushi Takabu, Kanagawa (JP)

(73) Assignee: KABUSHIKI KAISYA LEBEN, Kanagawa (JP)

( * ) Notice: Subject to any disclaimer, the term of this patent is extended or adjusted under 35 U.S.C. 154(b) by 191 days.

(21) Appl. No.: 17/421,506

(22) PCT Filed: Dec. 26, 2019

(86) PCT No.: PCT/JP2019/051230
§ 371 (c)(1),
(2) Date: Jul. 8, 2021

(87) PCT Pub. No.: WO2020/145185
PCT Pub. Date: Jul. 16, 2020

(65) Prior Publication Data
US 2022/0062623 A1    Mar. 3, 2022

(30) Foreign Application Priority Data

Jan. 9, 2019  (JP) ................................. 2019-001923

(51) Int. Cl.
*C09J 7/40* (2018.01)
*A61N 1/04* (2006.01)
(Continued)

(52) U.S. Cl.
CPC .............. *A61N 1/0496* (2013.01); *C09J 7/40* (2018.01); *C09J 201/00* (2013.01); *A61N 1/205* (2013.01); *C09J 2400/283* (2013.01)

(58) Field of Classification Search
CPC .. A61N 1/0496; A61N 1/205; A61N 1/36014; C09J 7/40; C09J 7/10; C09J 201/00; C09J 2400/283; A61F 13/02
See application file for complete search history.

(56) References Cited

U.S. PATENT DOCUMENTS

2008/0215128 A1* 9/2008 Rainey ................... A61N 1/205
602/53
2009/0088614 A1* 4/2009 Taub ................. A61B 5/14532
600/316
2018/0184939 A1* 7/2018 Christiansen ........ A61B 5/6833

FOREIGN PATENT DOCUMENTS

CN      201631918 U    11/2010
JP      H03-505047     11/1991
(Continued)

OTHER PUBLICATIONS

International Search Report of PCT/JP2019/051230, dated Feb. 4, 2020, 7 pages including English translation.
(Continued)

*Primary Examiner* — Ankit D Tejani
*Assistant Examiner* — Joshua Brendon Solomon
(74) *Attorney, Agent, or Firm* — Hamre, Schumann, Mueller & Larson, P.C.

(57) ABSTRACT

An adhesive sheet with flexibility for attaching a health appliance to a skin, including: a health appliance sticking portion which is a portion on which the health appliance is stuck; an adhesive portion for making the adhesive sheet adhere to the skin; first release paper stuck on the health appliance sticking portion in a peelable manner; and second release paper having an outer edge nearly identical to an outer edge of the adhesive portion in shape and size and stuck on the adhesive portion in a peelable manner so as to surround the first release paper, wherein the second release paper has stiffness that allows the second release paper to support the adhesive sheet and maintain a planar state in a state in which the first release paper is removed.

4 Claims, 8 Drawing Sheets

(51) Int. Cl.
*C09J 201/00* (2006.01)
*A61N 1/20* (2006.01)

(56) References Cited

FOREIGN PATENT DOCUMENTS

| | | |
|---|---|---|
| JP | H06-339531 | 12/1994 |
| JP | 3014312 U | 8/1995 |
| JP | 2005-296455 | 10/2005 |
| JP | 2006-043158 | 2/2006 |
| JP | 2006-320704 | 11/2006 |
| JP | 3129871 U | 3/2007 |
| JP | 2010-007026 | 1/2010 |
| JP | 2010-274056 | 12/2010 |
| JP | 2017-164191 | 9/2017 |
| JP | 2018-131584 | 8/2018 |
| JP | 3217444 U | 8/2018 |
| JP | 6423948 B1 | 11/2018 |
| WO | 2016/121499 | 8/2016 |
| WO | 2018/151474 | 8/2018 |

OTHER PUBLICATIONS

Office Action issued for Chinese Patent Application No. 201980091254.X, dated Aug. 11, 2022, 8 pages including machine translation.

\* cited by examiner

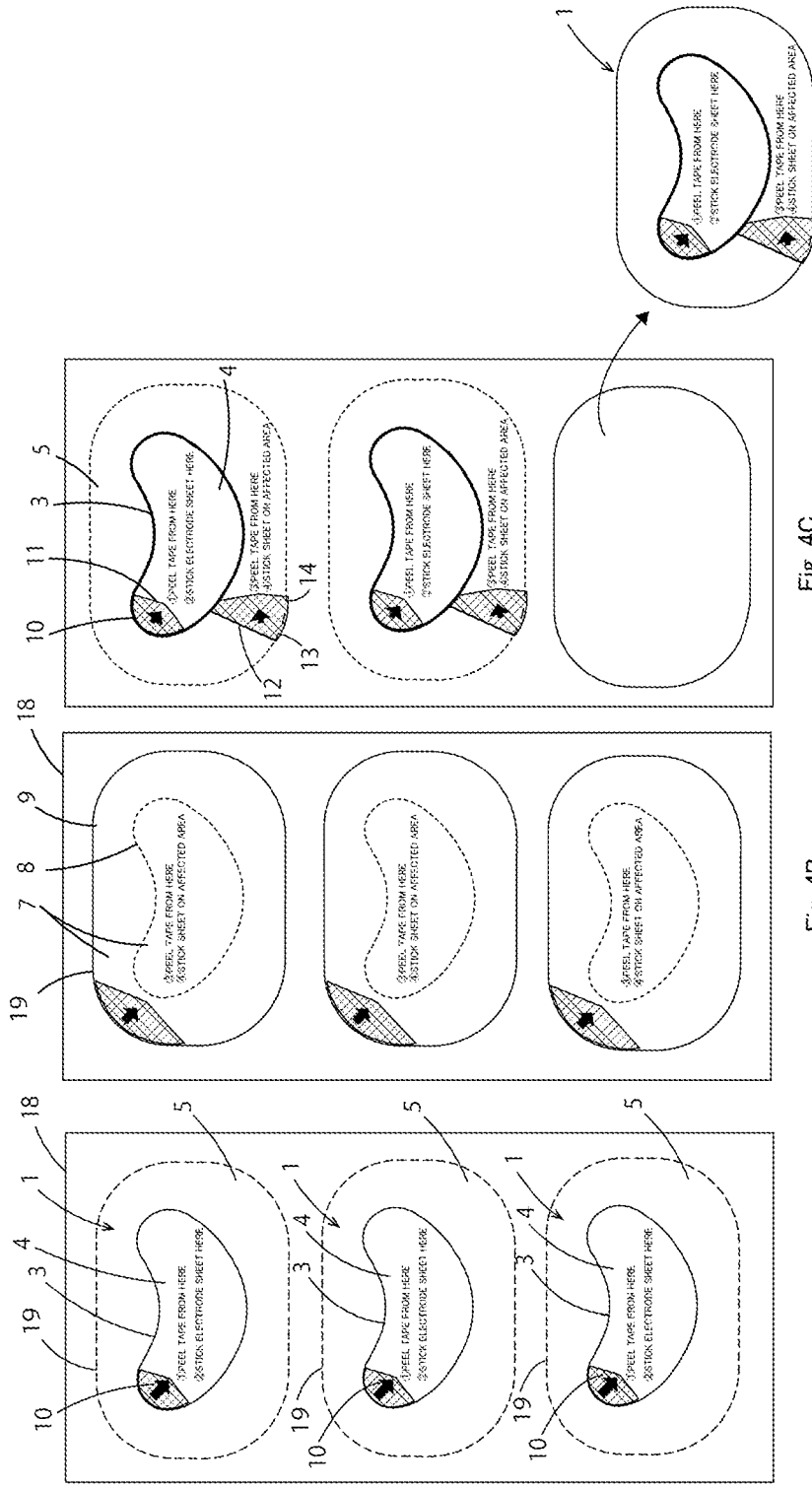

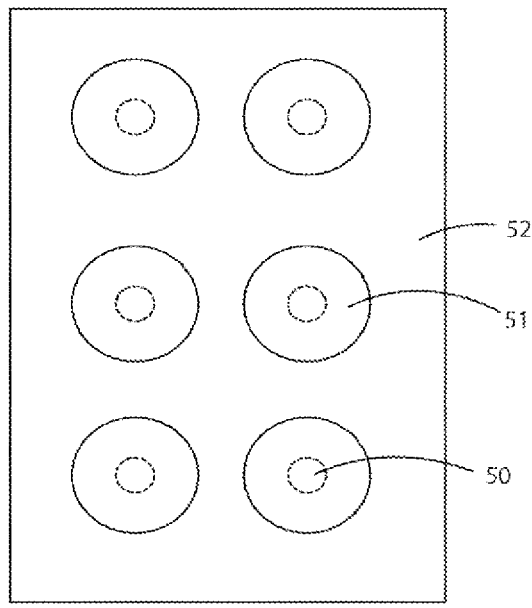
Fig. 11A – PRIOR ART
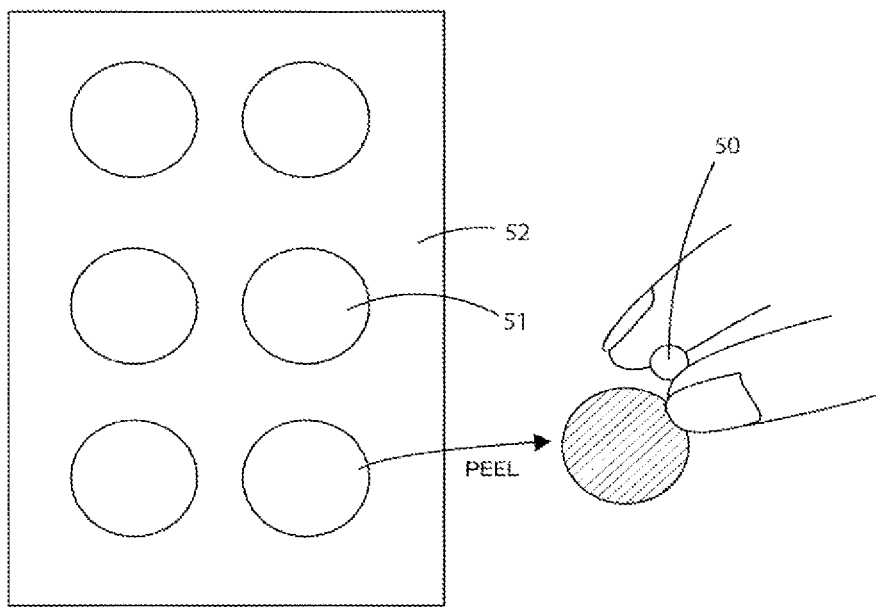
Fig. 11B – PRIOR ART

ADHESIVE SHEET

TECHNICAL FIELD

The present invention relates to an adhesive sheet that sticks a functional health appliance on the skin. The present invention claims priority to Japanese Patent Application No. 2019-001923, filed Jan. 9, 2019, and, in designated states where incorporation by literature reference is allowed, the contents of this application are incorporated herein by reference in their entirety.

BACKGROUND ART

In general, a health appliance that activates the function of the body by being brought into contact with a part of the body is widely used. As this health appliance, various health appliances are present and examples include a magnet, a needle or its equivalent, and the like.

It is usually necessary to bring these health appliances into contact with a part of the body and maintain this state. To achieve this state, an adhesive sheet has been widely used. The adhesive sheet is made of a flexible material and has, on one surface, an adhesive layer, which makes the adhesive sheet adhere to the skin with the health appliance sandwiched therebetween. By doing so, it is possible to bring the health appliance into intimate contact with the skin by the tension of the adhesive sheet.

The adhesive sheet in an unused state has an adhesive surface on which peelable release paper is stuck in order to protect the adhesive surface. The health appliance is sometimes provided between the adhesive sheet and the release paper in advance; in some cases, the health appliance is not provided therebetween in advance.

In FIG. 11, an adhesive sheet 51 and release paper 52 in a case where the health appliance is a magnet 50 are shown; FIG. 11(a) shows the state of the magnet 50 in an unused state and FIG. 11(b) shows a replacement adhesive sheet 51 and the state of the magnet 50 which is reused. In this example, as shown in FIG. 11(a), the magnet 50 is stuck on the peelable release paper 52 in a state in which the magnet 50 is placed at the center of an adhesive surface of the circular adhesive sheet 51. When used, the adhesive sheet 51 is peeled from the release paper 52 together with the magnet 50 and made to adhere to an affected area of the body.

In general, the magnet 50 tends to maintain the magnetized state for a long time, which makes it possible to reuse the magnet 50 even after the adhesive strength of the adhesive sheet 51 is reduced. For this reason, the replacement adhesive sheet 51 is also prepared. As for a poultice or the like, the poultice itself has adherence and is used by being applied to an affected area after release paper is peeled therefrom, and a replacement adhesive sheet is not usually used.

FIG. 11(b) shows the replacement adhesive sheet 51, release paper 52, and the magnet 50 which is reused. As shown in FIG. 11(b), the replacement adhesive sheet 51 is directly stuck on the release paper 52 without the magnet 50 sandwiched therebetween. When used, the adhesive sheet 51 is peeled from the release paper 52, and the magnet 50 is stuck on an adhesive surface of the adhesive sheet 51 and then stuck on the skin.

PTL 1 discloses a tape that is stuck on the skin, the tape which prevents a cuticle from being peeled, has sufficient holding power, and allows only a small amount of adhesive to remain when the tape is peeled.

CITATION LIST

Patent Literature

PTL 1: JP-A-2018-131584

SUMMARY OF INVENTION

Technical Problem

However, the adhesive sheet generally has a small degree of stretchability, has a small thickness of 0.1 to 0.5 mm, for example, and is very flexible. This sometimes causes the adhesive surfaces of the adhesive sheet to stick to each other when used. In particular, since the replacement adhesive sheet is a single body, when the adhesive sheet is peeled, the adhesive surfaces of the adhesive sheet itself often stick to each other due to warpage, movement, static electricity, or the like of the adhesive sheet.

Moreover, when the health appliance is a sheet-like health appliance having a large area such as a microcurrent sheet, the problem of the adhesive surfaces of the replacement adhesive sheet which stick to each other becomes pronounced.

It is to be noted that the microcurrent sheet is a health appliance that includes a positive electrode portion and a negative electrode portion having a potential difference therebetween and promotes health by making contact with the skin of a human and passing a microcurrent therethrough. The microcurrent sheet has a size of 10 to 250 mm, for example, in a maximum direction because the microcurrent sheet includes the above-described positive electrode portion and negative electrode portion.

An adhesive sheet for sticking this large sheet has a large area, which makes it difficult to hold the adhesive sheet such that adhesive surfaces do not stick to each other. In particular, the adhesive sheet has to be held alone when the adhesive sheet is replaced with another, which often causes adhesive surfaces to stick to each other unexpectedly.

Moreover, the problem is that it is difficult to stick the health appliance in a proper place on the replacement adhesive sheet.

Therefore, to solve at least one of the problems described above, an object of the present invention is to provide an adhesive sheet that is easily held such that adhesive surfaces do not stick to each other when used. Moreover, another object of the present invention is to provide an adhesive sheet that allows a health appliance to be easily stuck in a proper place.

Solution to Problem

To solve the problems described above, the present invention is an adhesive sheet with flexibility for attaching a health appliance which is repeatedly used more than once, for example, to a skin, including: a health appliance sticking portion which is a portion on which the health appliance is stuck; an adhesive portion for making the adhesive sheet adhere to the skin; first release paper stuck on the health appliance sticking portion in a peelable manner; and second release paper having an outer edge nearly identical in shape and size and stuck on the adhesive portion in a peelable manner so as to surround the first release paper, wherein the second release paper has stiffness that allows the second release paper to support the adhesive sheet and maintain a planar state in a state in which the first release paper is removed.

The first release paper or the health appliance sticking portion may have a shape matching at least a part of an outer shape of the health appliance. The first release paper and the second release paper may be separated from each other by a cut. The first release paper and the second release paper may each have a peel end in a peel start portion. The peel end may have a notch, a cut step portion, a folded portion, or an overlapping portion, which is provided in the peel start portion of each of the first release paper and the second release paper. The peel end may have a thin film piece provided in the peel start portion of each of the first release paper and the second release paper. The first release paper and the second release paper may be placed so as to be peeled in mutually opposite directions. The health appliance may be a sheet that is flexible, has a size of 10 to 250 mm in a maximum direction, and generates a microcurrent.

Advantageous Effects of Invention

According to the present invention, it is possible to obtain an adhesive sheet that can be held such that adhesive surfaces do not stick to each other when used. Moreover, according to the present invention, it is possible to obtain a replacement adhesive sheet that allows a health appliance to be easily stuck in a proper place.

BRIEF DESCRIPTION OF DRAWINGS

FIG. 4A to 4C show examples in which a plurality of adhesive sheets according to the embodiment of the present invention are formed on one mount.

FIG. 11A shows the state of a conventional adhesive sheet in an unused state and FIG. 11B shows the state of a magnet which is reused.

DESCRIPTION OF EMBODIMENTS

Hereinafter, embodiments which are application examples of the present invention will be described using the drawings.

Figure 1A:
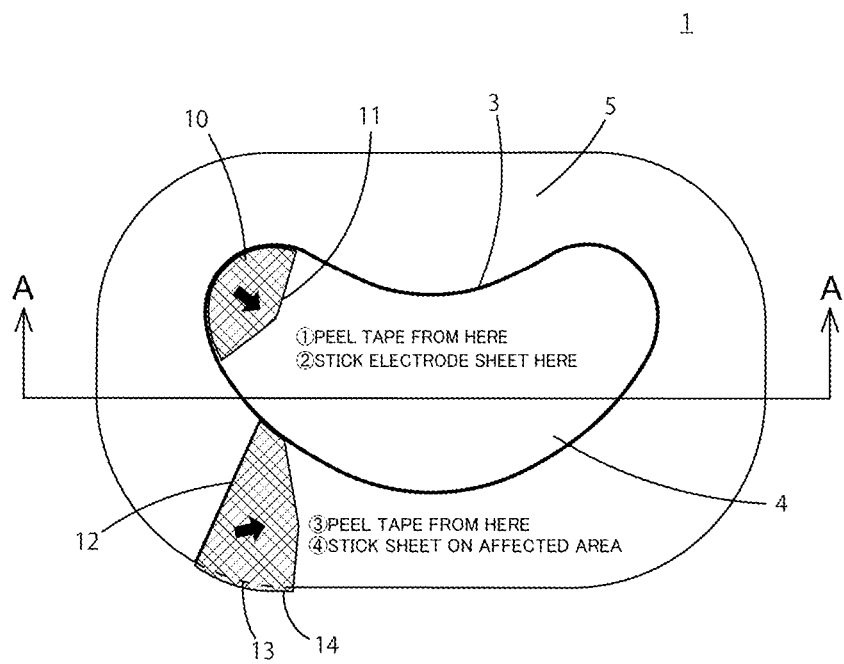
FIG. 1A is a plan view of an adhesive sheet according to one embodiment of the present invention and FIG. 1B is a cross-sectional view of the adhesive sheet.
Figure 1B:
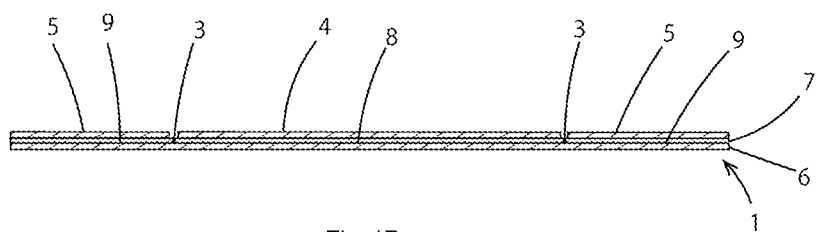

An adhesive sheet 1 according to one embodiment is shown in FIGS. 1A and 1B. FIG. 1A shows a plan view of the adhesive sheet 1. FIG. 1B shows a cross section of the adhesive sheet 1 when viewed in an arrow A-A direction of FIG. 1A.

The adhesive sheet 1 shown in FIGS. 1A and 1B is a replacement adhesive sheet. A state in which a health appliance is stuck thereon will be described later. In a state in which release paper is removed, the thickness of the adhesive sheet ranges, for example, from 0.03 to 0.5 mm (the thickness of the adhesive sheet including the release paper ranges from 0.1 to 1.0 mm and preferably from 0.1 to 0.6 mm). Moreover, the adhesive sheet has stretchability; it is preferable that, when stretched, the adhesive sheet has 110% stretchability, preferably 120% or more stretchability, and more preferably 130 to 180% stretchability compared to at least a state in which the adhesive sheet is not stretched. Examples of a material include polyester, cotton, wool, and silk and examples of a weave include a nonwoven fabric, a stretch woven fabric, and a knit fabric. The material may be a material that is stretched in one direction (for example, that is greatly stretched in a lateral direction) or a material that is greatly stretched in all directions.

In FIG. 1A, the adhesive sheet 1 is shown in a state in which release paper is stuck thereon. The release paper is divided into first release paper 4 and second release paper 5 by a cut 3. The first release paper 4 is placed roughly in the central part of the adhesive sheet 1. The second release paper 5 is placed on the periphery of the adhesive sheet 1 so as to surround the first release paper 4.

Various characters and figures are printed on upper surfaces of the first release paper 4 and the second release paper 5. The printed characters indicate directions for use in text form. Arrows, which are printed figures shown by way of example, indicate directions in which the first release paper 4 and the second release paper 5 are peeled. Numbers in the characters indicating the directions for use show the order of the directions for use. The method of use, the sequence of use, or the like is indicated only by the characters in this example; the method of use, the sequence of use, or the like may be indicated by peeled pictures, photographs, or the like or a combination thereof.

As shown in FIG. 1B, the adhesive sheet 1 includes an adhesive layer 7 on one surface of a flexible sheet 6. The first release paper 4 and the second release paper 5 are stuck on the adhesive layer 7.

The flexible sheet 6 can be formed by using a polymer film, a nonwoven fabric, cotton cloth, or the like. It is preferable to adopt a flexible and thin sheet as the flexible sheet 6 to alleviate a sense of discomfort which may be caused when the flexible sheet 6 is stuck on the skin. The adhesive layer 7 can be formed by using silicone, an acrylic-based pressure-sensitive adhesive (an acrylic-based tackiness agent), or the like. For the first release paper 4 and the second release paper 5, woodfree paper can be used as a base material and a silicone-based resin can be used as a release agent, or a laminate material including woodfree paper and resin can be used. Moreover, it is preferable that the flexible sheet 6 has water repellency and breathability, and a plurality of through holes may be provided for breathability.

The planar shape of the adhesive sheet 1 is almost the same as the shape of the first release paper 4 and the second release paper 5 which are combined together. The central part of the flexible sheet 6 is a health appliance sticking portion 8 on which a health appliance is stuck. The planar shape of the health appliance sticking portion 8 is nearly identical to the shape of the first release paper 4. An adhesive portion 9 is provided around the health appliance sticking portion 8. The planar shape of the adhesive portion 9 is nearly identical to the shape of the second release paper 5.

As will be described later, the health appliance sticking portion 8 is a region on which the health appliance is stuck. The adhesive portion 9 is an adhesive region for fixing the health appliance to the skin. Prior to shipment from a factory, the first release paper 4 is stuck on the adhesive layer 7 in the health appliance sticking portion 8. Moreover, the second release paper 5 is stuck on the adhesive layer 7 in the adhesive portion 9.

A peel start portion of the first release paper 4 is a peel end 10. The peel end 10 of the present embodiment has a thin film piece 11. The thin film piece 11 is a film connected to an edge of the peel end 10 and can be pulled like a tab when the first release paper 4 is peeled.

It is to be noted that the peel end 10 may have no additional part like the thin film piece 11 and may be provided as an end having a shape that allows the end to be easily peeled. For example, the end having a shape that allows the end to be easily peeled may be an end with a notch that can be easily caught by a fingernail or may be an end with a folded portion that can be easily pulled by fingers.

The second release paper 5 has a peel end 13 formed by a cut 12 in an approximately radial direction. A thin film piece 14 is connected to an edge of the peel end 13 of the present embodiment. The thin film piece 14 is a film that can be pulled when the second release paper 5 is peeled. Moreover, as in the case of the peel end 10, the peel end 13 may have no additional part like the thin film piece 14 and may be an end having a shape that allows the end to be easily peeled, such as a notch that can be easily caught by a fingernail or a folded portion that can be easily pulled by fingers. Furthermore, a peel start portion may be indicated by print. The peel start portion shown here is one example and is not necessarily limited to this position.

Figure 2A:
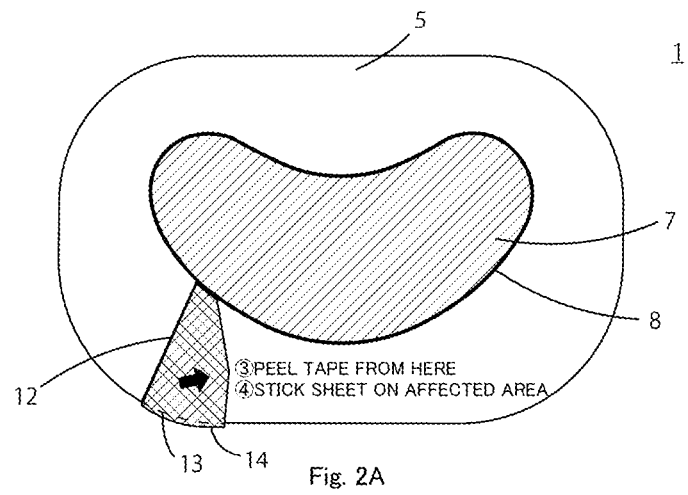
FIG. 2A to 2C are explanatory diagrams explaining, in chronological order, directions for use of the adhesive sheet according to the embodiment of the present invention.
Figure 2B:
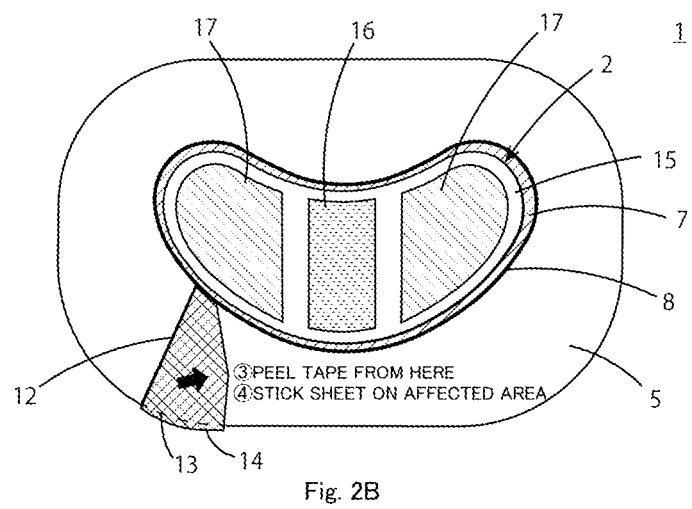
Figure 2C:
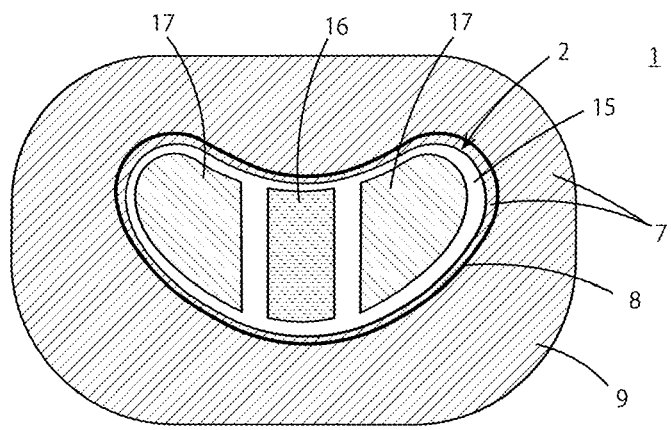

FIG. 2A to 2C illustrate explanatory diagrams showing, in chronological order, directions for use of the adhesive sheet 1 according to the present embodiment. At the start of use of the adhesive sheet 1, the first release paper 4 is peeled. FIG. 2A shows a state in which the first release paper 4 (see FIG. 1) is removed. As shown in FIG. 2A, the adhesive layer 7 is exposed in an area where the first release paper 4 was removed, and this area serves as the health appliance sticking portion 8 on which the health appliance is stuck.

Next, the health appliance is stuck on the health appliance sticking portion 8. In the present embodiment, an example in which the health appliance is a microcurrent sheet 2 which generates a microcurrent is shown.

The thickness of the microcurrent sheet 2 ranges, for example, from 1 to 8 mm and preferably from 1.5 to 6 mm. A material for a base of the microcurrent sheet 2 is a flexible plastic material such as silicone rubber, an elastomer, vinyl chloride, nylon, ABS, or polypropylene.

Alternatively, a sponge material may be used.

Alternatively, the microcurrent sheet may be made of cloth with metal fiber inserted thereinto.

Furthermore, for example, a moisturizer, beauty essence, vitamin, hormone, or the like may be applied in sheet form to the microcurrent sheet 2 or a film-like object impregnated therewith may be stacked on the microcurrent sheet 2, such that the microcurrent sheet 2 serves as a functional penetration implement that promotes penetration through the skin.

As shown in FIG. 2B, the microcurrent sheet 2 includes an insulating sheet 15 and includes positive electrode foil 16 and negative electrode foil 17 on the insulating sheet 15. The positive electrode foil 16 is provided in the central part of the microcurrent sheet 2, and the negative electrode foil 17 is provided on both sides of the positive electrode foil 16. The positive electrode foil 16 includes a portion acting as a positive electrode by making contact with the skin, the negative electrode foil 17 includes a portion acting as a negative electrode by making contact with the skin, and the insulating sheet 15 provides isolation between the positive electrode and the negative electrode on the skin side. The positive electrode foil 16 and the negative electrode foil 17 are electrically connected. The insulating sheet 15 is formed in the form of a sheet and is provided with a plurality of window portions passing therethrough in a thickness direction. The positive electrode foil 16 and the negative electrode foil 17 are exposed on the skin side through these window portions and serve as the positive electrode and the negative electrode, respectively.

The microcurrent sheet 2 includes a base sheet (which is not shown in the drawing) similar to the whole of the microcurrent sheet 2 in shape, the negative electrode foil 17 which is also approximately similar to the whole of the microcurrent sheet 2 in shape and stacked on the base sheet, the positive electrode foil 16 stacked on the negative electrode foil 17 only roughly in the center thereof, and a window insulating sheet 2 which has three window portions passing therethrough and is stacked on the positive electrode foil 16. Each electrode foil is formed as a thin film by plating or rolling. The negative electrode foil 17 is aluminum, titanium, zinc, or the like, the positive electrode foil 16 is, for example, precious metal such as gold or silver, and they generate a microcurrent by a difference in ionization tendency. The microcurrent sheet 2 has flexibility so as to be able to flexibly follow a curved surface of the body. The thickness of the microcurrent sheet 2 ranges, for example, from 1 to 8 mm and preferably from 1.5 to 6 mm. A material for the base of the small electrode sheet 2 is a flexible plastic material such as silicone rubber, an elastomer, vinyl chloride, nylon, ABS, or polypropylene.

Moreover, in addition to a plate-like shape, the microcurrent sheet 2 may have a net-like shape with breathability in which a plurality of holes are provided. Furthermore, the microcurrent sheet 2 may be formed so as to include cloth thereof.

The planar shape of the health appliance sticking portion 8 has a shape matching at least a part of the outer shape of the microcurrent sheet 2. It goes without saying that the planar shape of the health appliance sticking portion 8 may be almost the same as the outer shape of the microcurrent sheet 2.

According to the present embodiment, before the microcurrent sheet 2 is stuck on the health appliance sticking portion 8, as shown in FIG. 2B, the adhesive sheet 1 is in a state in which the first release paper 4 is removed therefrom and only the second release paper 5 is stuck on the adhesive sheet 1. In the present embodiment, the second release paper 5 can support the adhesive sheet 1 and maintain the planar state in a state in which the first release paper 4 is removed.

That is, the woodfree paper and the resin, which is a coating or a layer stacked on the woodfree paper, of the second release paper 5 and the total stiffness of the flexible sheet 6 provide some degree of resistance to bend, and the second release paper 5 serves as a frame of the health appliance sticking portion 8. This allows the adhesive sheet 1 to maintain the planar state even with some bend. Since the second release paper 5 supports, like a frame, the perimeter of an adhesive surface of the health appliance sticking portion 8, adhesive surfaces do not stick to each other in the health appliance sticking portion 8. Moreover, at this stage, the second release paper 5 covers the adhesive surface, which makes it possible to prevent the adhesive surface from sticking to fingers when the adhesive sheet 1 is held or picked up with the fingers.

That is, according to the present embodiment, it is possible to prevent the adhesive surfaces of the adhesive sheet 1 from sticking to each other and easily stick the microcurrent sheet 2 thereon.

Moreover, in the present embodiment, since the planar shape of the health appliance sticking portion 8 is almost the same as the outer shape of the microcurrent sheet 2, by sticking the microcurrent sheet 2 in this area, it is possible to stick the microcurrent sheet 2 in a proper place smoothly.

After the microcurrent sheet 2 is stuck on the health appliance sticking portion 8, the second release paper 5 is removed. FIG. 2C shows a state in which the microcurrent sheet 2 is stuck and the second release paper 5 is removed.

In this state, the microcurrent sheet 2 supports the adhesive sheet 1 and can maintain the adhesive sheet 1 in the planar state. Moreover, since the adhesive portion 9 is present around the microcurrent sheet 2, the adhesive surfaces of the adhesive portion 9 do not stick to each other. Thus, in the state of FIG. 2C, the adhesive sheet 1 and the microcurrent sheet 2 can be easily stuck in a desired area of the body.

Figure 3A:
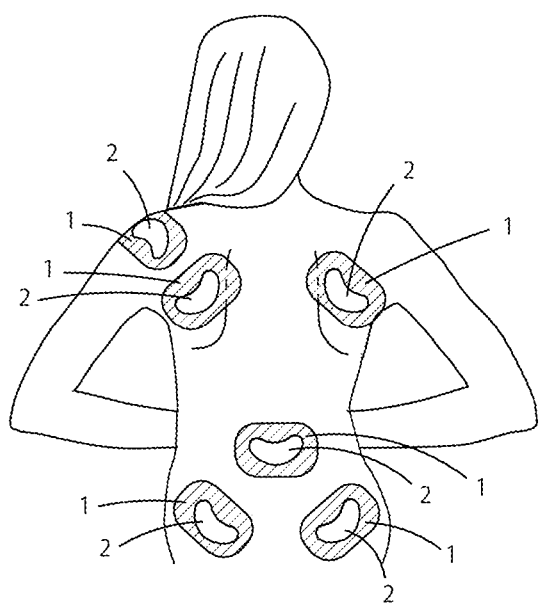
FIG. 3A to 3E are explanatory diagrams illustrating a state in which the adhesive sheet according to the embodiment of the present invention is used.
Figure 3C:
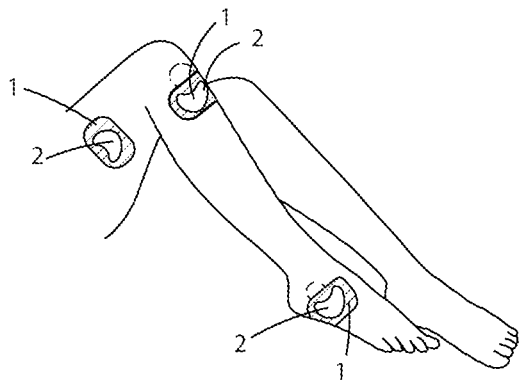
Figure 3D:
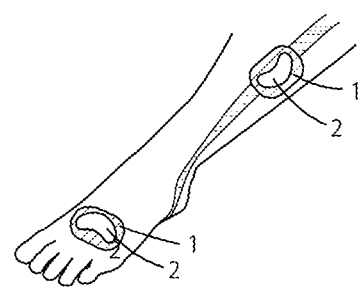
Figure 3B:
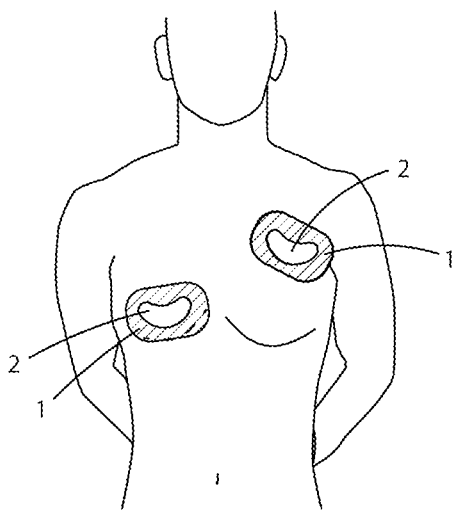
Figure 3E:
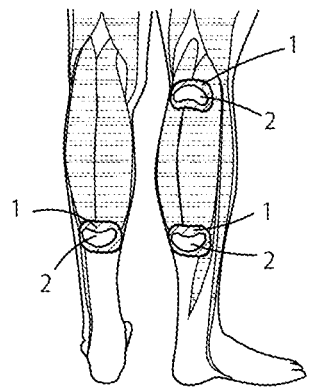

FIG. 3A to 3C are diagrams illustrating a state in which the adhesive sheet 1 according to the present embodiment is used. FIG. 3A shows a state in which the adhesive sheet 1 and the microcurrent sheet 2 are stuck on the shoulder, the shoulder blades, and the lower back. FIG. 3B shows a state in which the adhesive sheet 1 and the microcurrent sheet 2 are stuck on an upper left area and a lower right area of the chest. FIG. 3C shows a state in which the adhesive sheet 1 and the microcurrent sheet 2 are stuck on the thigh, the knee, and a lower part of the ankle. FIG. 3D shows a state in which the adhesive sheet 1 and the microcurrent sheet 2 are stuck on the shin and the instep. FIG. 3E shows a state in which the adhesive sheet 1 and the microcurrent sheet 2 are stuck on an upper part of the calf and lower parts of the calves.

According to the present embodiment, it is possible to easily stick the adhesive sheet 1 and the microcurrent sheet 2 in the sticking areas of the body shown in the drawing. Unlike a hard and small magnet therapeutic instrument, the microcurrent sheet 2 has an area which is large to some extent; however, the microcurrent sheet 2 is flexible, which allows the microcurrent sheet 2 to flexibly follow even a curved surface of a sticking area. Moreover, since the adhesive sheet 1 is also flexible, it is possible to maintain the stuck state in a state in which the microcurrent sheet 2 is made to flexibly follow a sticking area.

FIG. 4A to 4C show cases where a plurality of adhesive sheets 1 are formed on one mount 18. FIG. 4A and FIG. 4B show the back side with release paper and the front side with the adhesive sheets 1, respectively, in a factory shipment state. FIG. 4B shows a state viewed from the front side, and a cut 19 is provided around each adhesive sheet 1. The cut 19 does not reach the release paper side.

The mount 18 is obtained by providing, on a rectangular flexible sheet, an adhesive layer and sticking release paper thereon. The flexible sheet, the adhesive layer, and the release paper of the mount 18 respectively correspond to the flexible sheet 6, the adhesive layer 7, and the first release paper 4 and the second release paper 5 of FIGS. 1A and 1B. A cut 3 formed in an intermittent manner (such as perforations) is provided around the first release paper 4 of the mount 18. The cut 3 is formed only in the mount 18 and does not reach the adhesive sheet 1. Each adhesive sheet 1 may be configured so as to be removed from the mount 18 by being detached along the cut 19.

A method of use is as follows. The first release paper 4 is peeled from the back side of FIG. 4A by the cut 3, and the microcurrent sheet is stuck with the electrode surface facing outward. Then, the adhesive sheet 1 is peeled from the second release paper 5 (which is also the mount 18) from the front side of FIG. 4B (meanwhile, the microcurrent sheet functions as a core material and prevents the adhesive portions 9 surrounding it from sticking to each other). Furthermore, the peeled adhesive sheet 1 is stuck on an affected area. This is the end of a procedure. FIG. 4C shows a state in which each adhesive sheet 1 is removed along perforations or the like for explanatory convenience. Under normal circumstances, the adhesive sheet 1 is detached from the mount 18 on a one-by-one basis and used by the method shown in FIG. 2A to 2C. Alternatively, on the mount 18, the first release paper 4 and the second release paper 5 may be peeled, the microcurrent sheet 2, which is not shown in the drawing, may be stuck on the adhesive sheet 1, and the adhesive sheet 1 may be removed from the mount 18 and used.

The present embodiment has an advantage in that it is suitable for the mass production of the adhesive sheets 1 and it prevents the adhesive sheets 1 from getting separated and allows the user to manage them easily.

Figure 5A:
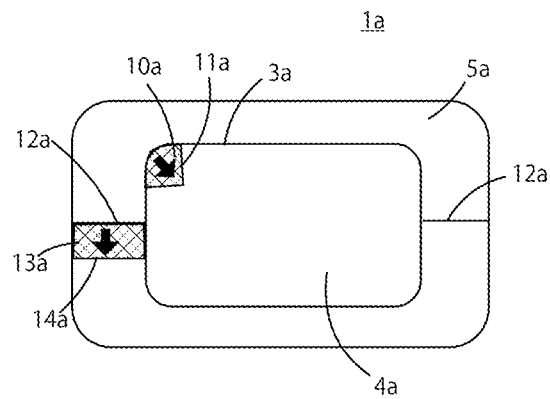
FIG. 5A is a plan view of the adhesive sheet according to the embodiment of the present invention and FIG. 5B is a diagram showing a state in which second release paper is removed.
Figure 5B:
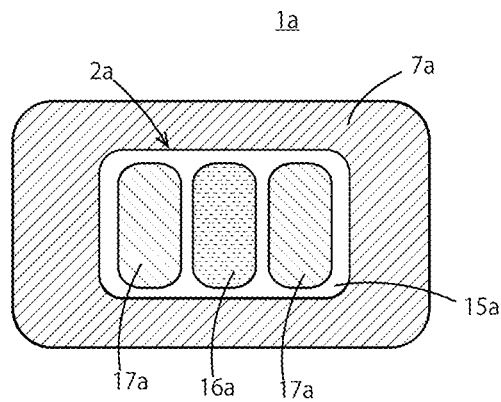

FIGS. 5A and 5B show an adhesive sheet 1a of another embodiment. The adhesive sheet 1a of the present embodiment has an approximately rectangular shape which is oblong. First release paper 4a is placed in the central part of the adhesive sheet 1a, and second release paper 5a is placed around the first release paper 4a so as to surround it. The first release paper 4a and the second release paper 5a are separated from each other by a cut 3a.

One corner portion of the first release paper 4a is a peel end 10a. The peel end 10a has a thin film piece 11a, which allows the peel end 10a to be easily peeled. It is to be noted that the thin film piece 11a can be appropriately omitted. The second release paper 5a has a pair of cuts 12a, which allows the second release paper 5a to be separated into two parts and peeled. A peel end 13a is formed at an end of one peeled part of the second release paper 5a. The peel end 13a has a thin film piece 14a, which allows the peel end 13a to be easily peeled. The thin film piece 14a can be appropriately omitted. When used, the first release paper 4a is first peeled and a microcurrent sheet 2a is stuck on that portion. Then, the second release paper 5a is removed.

FIG. 5B shows a state in which the microcurrent sheet 2a is stuck and the second release paper 5a is removed. The microcurrent sheet 2a has a shape which is nearly identical to that of the first release paper 4a, includes positive electrode foil 16a in the central part of an insulating sheet 15a, and includes negative electrode foil 17a on both sides of the positive electrode foil 16a. An adhesive layer 7a is present around the microcurrent sheet 2*a*, which makes it possible to easily fix the microcurrent sheet 2*a* to the skin.

Also in the present embodiment, in a state in which the first release paper 4*a* is removed, the second release paper 5*a* allows the adhesive sheet 1*a* to maintain the planar state and can prevent adhesive surfaces from sticking to each other. Moreover, the microcurrent sheet 2*a* only has to be stuck on a portion from which the first release paper 4*a* was removed, which makes it possible to easily stick the microcurrent sheet 2*a* in a proper place.

Figure 6A:
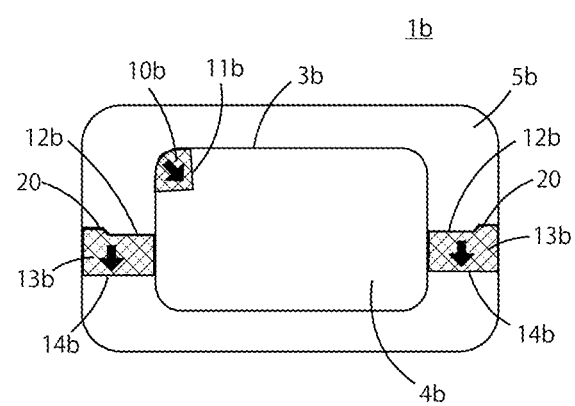
FIG. 6A is a plan view of an adhesive sheet according to another embodiment of the present invention and FIG. 6B is a diagram showing a state in which second release paper is removed.
Figure 6B:
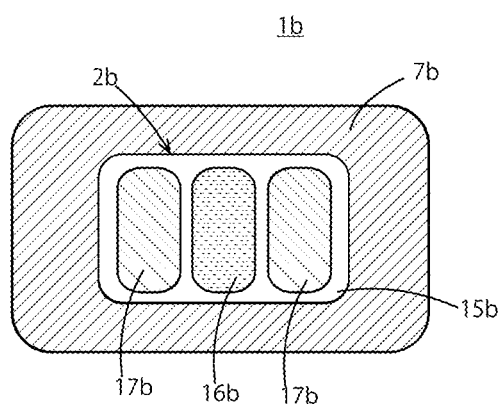

FIGS. 6A and 6B show an adhesive sheet 1*b* of another embodiment. The adhesive sheet 1*b* of the present embodiment also has an approximately rectangular shape which is oblong. First release paper 4*b* is placed in the central part of the adhesive sheet 1*b*, and second release paper 5*b* is placed around the first release paper 4*b* so as to surround it. The first release paper 4*b* and the second release paper 5*b* are separated from each other by a cut 3*b*.

One corner portion of the first release paper 4*b* is a peel end 10*b*. The peel end 10*b* has a thin film piece 11*b*, which allows the peel end 10*b* to be easily peeled. The thin film piece 11*b* can be appropriately omitted. The second release paper 5*b* has a pair of cuts 12*b*, which allows the second release paper 5*b* to be separated into two parts and peeled. Peel ends 13*b* are formed at both ends of one peeled part of the second release paper 5*b*. Each peel end 13*b* has a thin film piece 14*b*, which allows the peel end 13*b* to be easily peeled. It is to be noted that the thin film piece 14*b* can be appropriately omitted. Moreover, a cut line may be indicated by, for example, distinguishing this portion from other portions by using different colors.

The cut 12*b* of the present embodiment characteristically has a cut step portion 20. The presence of the cut step portion 20 makes a corner of the peel end 13*b* protrude when the adhesive sheet 1*b* is folded along the cut 12*b*, which makes it possible to pull the corner with fingers. This makes it possible to remove the second release paper 5*b* with ease. When used, the first release paper 4*b* is first peeled and a microcurrent sheet 2*b* is stuck on that portion. Then, the second release paper 5*b* is removed.

FIG. 6B show a state in which the microcurrent sheet 2*b* is stuck and the second release paper 5*b* is removed. The microcurrent sheet 2*b* has a shape which is nearly identical to that of the first release paper 4*b*, includes positive electrode foil 16*b* in the central part of an insulating sheet 15*b*, and includes negative electrode foil 17*b* on both sides of the positive electrode foil 16*b*. An adhesive layer 7*b* is present around the microcurrent sheet 2*b*, which makes it possible to easily fix the microcurrent sheet 2*b* to the skin. Also in the present embodiment, it is possible to obtain effects similar to those described above.

Figure 7A:
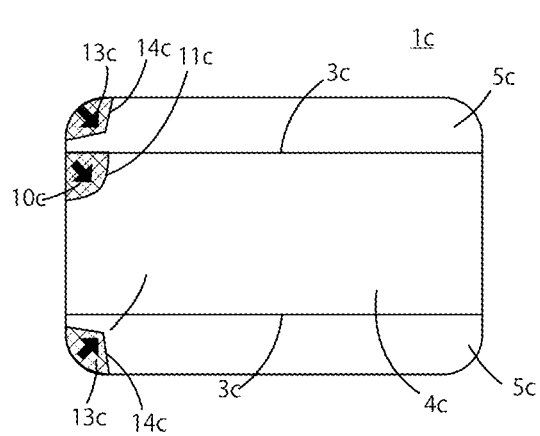
FIG. 7A is a plan view of an adhesive sheet according to another embodiment of the present invention and FIG. 7B is a diagram showing a state in which second release paper is removed.
Figure 7B:
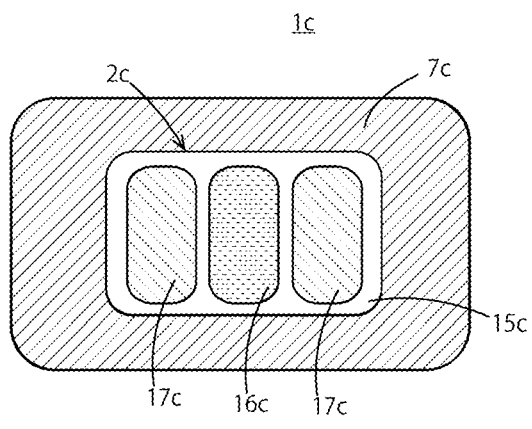

FIGS. 7A and 7B show an adhesive sheet 1*c* of another embodiment. The adhesive sheet 1*c* of the present embodiment also has an approximately rectangular shape which is oblong. First release paper 4*c* is provided so as to pass through the adhesive sheet 1*c* from the central part of one side of the adhesive sheet 1*c* almost parallel to the other sides thereof.

Second release paper 5*c* is placed on both sides of the first release paper 4*c*. The first release paper 4*c* and the second release paper 5*c* are separated from each other by a cut 3*c*. One corner portion of the first release paper 4*c* is a peel end 10*c*. The peel end 10*c* has a thin film piece 11*c*, which allows the peel end 10*c* to be easily peeled. Two pieces of second release paper 5*c* are present on both sides of the first release paper 4*c*, and a peel end 13*c* is provided at an end of each piece. The peel end 13*c* has a thin film piece 14*c*, which allows the peel end 13*c* to be easily peeled.

When the adhesive sheet 1*c* is folded along the cut 3*c*, the peel end 10*c* or the peel end 13*c* of the present embodiment separates from an adhesive layer 7*c*, which makes it easy to peel the peel end 10*c* or the peel end 13*c*. When used, the first release paper 4*c* is first peeled and a microcurrent sheet 2*c* is stuck on a central portion thereof. Then, the second release paper 5*c* is removed.

FIG. 7B shows a state in which the microcurrent sheet 2*c* is stuck and the second release paper 5*c* is removed. The microcurrent sheet 2*c* has a rectangular shape, includes positive electrode foil 16*c* in the central part of an insulating sheet 15*c*, and includes negative electrode foil 17*c* on both sides of the positive electrode foil 16*c*. The adhesive layer 7*c* is present around the microcurrent sheet 2*c*, which makes it possible to easily fix the microcurrent sheet 2*c* to the skin. Also in the present embodiment, it is possible to obtain effects similar to those described above.

Figure 8A:
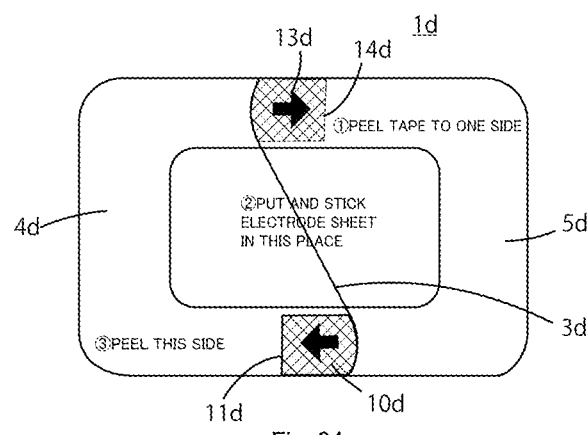
FIG. 8A is a plan view of an adhesive sheet according to another embodiment of the present invention.
Figure 8B:
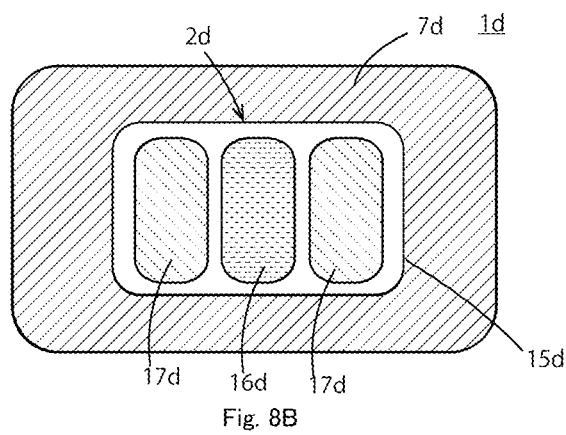
FIG. 8B is a diagram showing a state in which second release paper is removed.
Figure 8C:
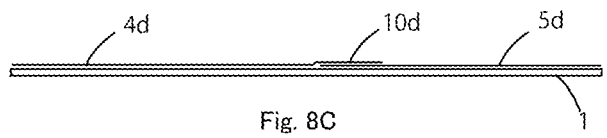
FIG. 8C is a diagram showing a modified example.

FIG. 8A to 8C show an adhesive sheet 1*d* of another embodiment. The adhesive sheet 1*d* of the present embodiment also has an approximately rectangular shape which is oblong. However, in the present embodiment, first release paper 4*d* covers roughly the left half of the adhesive sheet 1*d* and second release paper 5*d* covers roughly the right half of the adhesive sheet 1*d*.

The first release paper 4*d* and the second release paper 5*d* are separated from each other by a cut 3*d*. The cut 3*d* is provided such that one corner portion of each of the first release paper 4*d* and the second release paper 5*d* protrudes into the other side so as to make it easy to peel the first release paper 4*d* and the second release paper 5*d*. A protruding end of the first release paper 4*d* is a peel end 10*d*. The peel end 10*d* has a thin film piece 11*d*. A protruding end of the second release paper 5*d* is a peel end 13*d*. The peel end 13*d* has a thin film piece 14*d*.

FIG. 8C shows a modified example of the peel end 10*d*. As shown in FIG. 8C, the peel end 10*d* or the peel end 13*d* may be an overlapping portion that protrudes toward the other release paper and overlaps with the release paper on the other side.

As indicated by arrows printed on the thin film piece 11*d* and the peel end 13*d* of FIG. 8A, the first release paper 4*d* and the second release paper 5*d* of the present embodiment are peeled in mutually opposite directions. The first release paper 4*d* and the second release paper 5*d* are peeled in opposite directions, which makes it possible to peel them easily. FIG. 8B shows a state in which the first release paper 4*d* and the second release paper 5*d* are removed and a microcurrent sheet 2*d* is stuck.

The microcurrent sheet 2*d* has a rectangular shape, includes positive electrode foil 16*d* in the central part of an insulating sheet 15*d*, and includes negative electrode foil 17*d* on both sides of the positive electrode foil 16*d*. An adhesive layer 7*d* is present around the microcurrent sheet 2*d*, which makes it possible to easily fix the microcurrent sheet 2*d* to the skin. Also in the present embodiment, in a state in which the first release paper 4*d* is removed, the second release paper 5*d* allows the adhesive sheet 1*d* to maintain the planar state and can prevent adhesive surfaces from sticking to each other. The same applies to a case where the second release paper 5*d* is first removed.

Figure 9A:
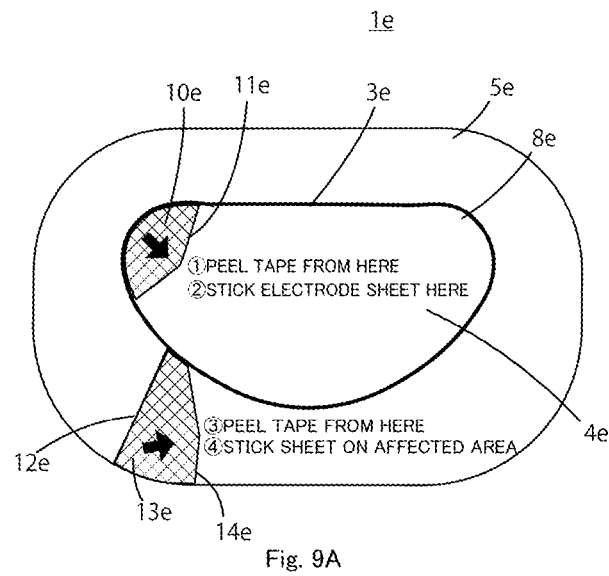
FIG. 9A is a plan view of an adhesive sheet according to another embodiment of the present invention and FIG. 9B is a diagram showing a microcurrent sheet.
Figure 9B:
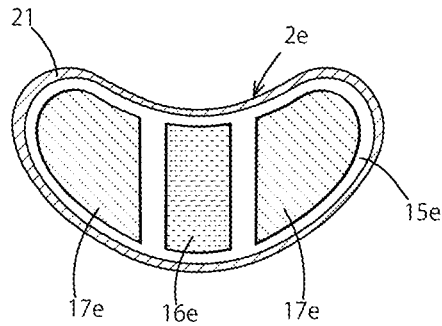

FIGS. 9A and 9B show an adhesive sheet 1*e* according to another embodiment. In the present embodiment, a health appliance sticking portion 8*e* has a shape matching at least a part of the outer shape of a health appliance. It is to be noted that, in FIGS. 9A and 9B, a portion which is the same as that of FIGS. 1A and 1B is denoted by a reference sign which is the same as that used in FIGS. 1A and 1B, and overlapping explanations are sometimes omitted.

The adhesive sheet 1e of the present embodiment also has an approximately rectangular shape which is oblong. First release paper 4e is placed in the central part of the adhesive sheet 1e, and second release paper 5e is placed around the first release paper 4e so as to surround it. The first release paper 4e and the second release paper 5e are separated from each other by a cut 3e.

One corner portion of the first release paper 4e is a peel end 10e. The peel end 10e has a thin film piece 11e which can be omitted. The second release paper 5e has a cut 12e, which allows the second release paper 5e to be peeled therefrom. One end near the cut 12e of the second release paper 5e is a peel end 13e. The peel end 13e has a thin film piece 14e which can be omitted.

The health appliance sticking portion 8e of the adhesive sheet 1e is covered with the first release paper 4e and has the same shape as the first release paper 4e. As shown in FIG. 9A, the health appliance sticking portion 8e is approximately half-moon shaped. By contrast, as shown in FIG. 9B, a microcurrent sheet 2e, which is the health appliance, is approximately crescent-shaped.

That is, only a part (a lower part) of the outer shape of the health appliance sticking portion 8e matches that of the microcurrent sheet 2e. However, as illustrated in this example, when the part of the outer shape of the health appliance sticking portion 8e and the part of the outer shape of the microcurrent sheet 2e, which match each other, clearly suggest a proper matching state of the health appliance sticking portion 8e and the microcurrent sheet 2e, it is possible to easily stick the microcurrent sheet 2e in a proper place. In this example, by removing the first release paper 4e and then aligning the lower part of the microcurrent sheet 2e with the lower part of the outer shape of the health appliance sticking portion 8e, it is possible to easily stick the microcurrent sheet 2e in a proper place.

It is to be noted that the microcurrent sheet 2e includes positive electrode foil 16e in the central part of an insulating sheet 15e and includes negative electrode foil 17e on both sides of the positive electrode foil 16e. The microcurrent sheet 2e includes an adhesive layer 21 on the periphery thereof; the adhesive layer 21 can be omitted.

Also in the present embodiment, the second release paper 5e has the effect of supporting the adhesive sheet 1e after the first release paper 4e is removed and maintaining the planar state.

Figure 10A:
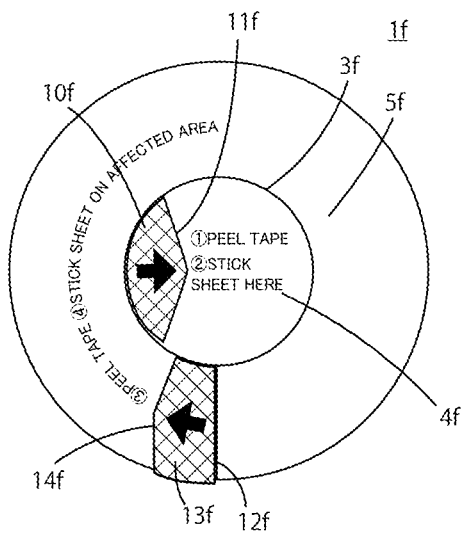
FIG. 10A is a plan view of an adhesive sheet according to another embodiment of the present invention and FIG. 10B is a diagram showing a state in which second release paper is removed.
Figure 10B:
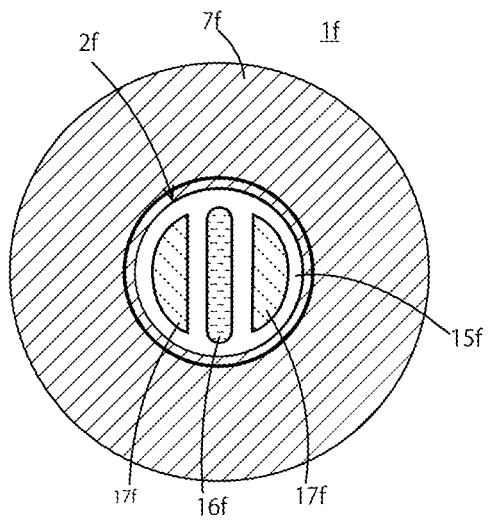

FIGS. 10A and 10B show an adhesive sheet 1f of another embodiment. The adhesive sheet 1f of the present embodiment has an approximately circular shape. First release paper 4f is placed in the central part of the adhesive sheet 1f and has a circular shape. Second release paper 5f is placed in a concentric manner with respect to the first release paper 4f and is placed around the first release paper 4f. The first release paper 4f and the second release paper 5f are separated from each other by a cut 3f.

A part of a circumferential portion of the first release paper 4f is a peel end 10f. The peel end 10f has a thin film piece 11f. The second release paper 5f has a cut 12f in a radial direction, which allows the second release paper 5f to be peeled therefrom. A peel end 13f is formed at an end near the cut 12f. The peel end 13f has a thin film piece 14f. When used, the first release paper 4f is first peeled and a microcurrent sheet 2f is stuck on that portion.

FIG. 10B shows a state in which the microcurrent sheet 2f is stuck and the second release paper 5f is removed. The microcurrent sheet 2f has a circular shape, includes positive electrode foil 16f in the central part of an insulating sheet 15f, and includes negative electrode foil 17f on both sides of the positive electrode foil 16f. An adhesive layer 7f is present around the microcurrent sheet 2f, which makes it possible to easily fix the microcurrent sheet 2f to the skin.

Also in the present embodiment, in a state in which the first release paper 4f is removed, the second release paper 5f can maintain the adhesive sheet 1f in the planar state and prevent adhesive surfaces from sticking to each other. Moreover, the microcurrent sheet 2f only has to be stuck on a circular portion from which the first release paper 4f was removed, which makes it possible to easily stick the microcurrent sheet 2f in a proper place.

While the above description deals with a replacement adhesive sheet, an adhesive sheet having the same structure as the adhesive sheet described above and having a health appliance mounted thereon in advance can be shipped from the factory. In this case, it is only necessary to stick the health appliance on the health appliance sticking portion of the adhesive sheet and stick the release paper thereon. Thus, the adhesive sheets described in the above embodiments are not limited to replacement adhesive sheets and include an adhesive sheet with a health appliance mounted thereon.

While a person skilled in the art may be able to conceive of additional effects or various modifications based on the description given above, embodiments of the present invention are not limited to the embodiments described above. Various additions, changes, and partial elimination may be made without departing from the conceptual idea and spirit of the present invention which are derived from the subject matter recited in the claims and its equivalents.

REFERENCE SIGNS LIST

1: adhesive sheet
2: microcurrent sheet
3: cut
4: first release paper
5: second release paper
6: flexible sheet
7: adhesive layer
8: health appliance sticking portion
9: adhesive portion
10: peel end
11: thin film piece
15: insulating sheet
16: positive electrode foil
17: negative electrode foil
18: mount
20: cut step portion
50: magnet
52: release paper

The invention claimed is:

1. A replacement adhesive sheet with flexibility for attaching a health appliance to a skin, comprising:
   an adhesive layer with a health appliance sticking portion which is a portion on which the health appliance is intended to be stuck;
   the adhesive layer further includes an adhesive portion for making the replacement adhesive sheet adhere to the skin, the health appliance sticking portion and the adhesive portion are located on a same side of the adhesive layer;
   first release paper stuck on the health appliance sticking portion in a peelable manner; and second release paper separate from the first release paper and having an outer edge nearly identical to an outer edge of the adhesive portion in shape and size and stuck on the adhesive portion in a peelable manner so as to surround the first release paper, wherein the second release paper has stiffness that allows the second release paper to support the adhesive sheet and maintain a planar state in a state in which the first release paper is removed, and the first release paper and the second release paper are located on the same side of the adhesive layer.

2. The replacement adhesive sheet according to claim 1, wherein the first release paper or the health appliance sticking portion has a shape matching at least a part of an outer shape of the health appliance.

3. The replacement adhesive sheet according to claim 1, wherein the first release paper is in direct contact with the health appliance sticking portion.

4. The replacement adhesive sheet according to claim 1, wherein the health appliance is not disposed between the first release paper and the health appliance sticking portion.

* * * * *